United States Patent [19]

Levy et al.

[11] 4,067,005

[45] Jan. 3, 1978

[54] INVALID BED SYSTEM

[76] Inventors: Joshuah Levy; Isaac Levy, both of 802 Ave. "N"; Frank H. Klein, 614 Ave. "J", all of Brooklyn, N.Y. 11230

[21] Appl. No.: 731,366

[22] Filed: Oct. 12, 1976

Related U.S. Application Data

[63] Continuation-in-part of Ser. No. 572,720, April 29, 1975, abandoned.

[51] Int. Cl.² .............................................. G08B 21/00
[52] U.S. Cl. .......................................... 340/279; 5/92; 200/85 R; 340/272; 362/130
[58] Field of Search ............... 340/279, 272, 311, 312; 5/92; 240/4; 200/85 R

[56] References Cited

U.S. PATENT DOCUMENTS

| | | | |
|---|---|---|---|
| 299,649 | 6/1884 | Keep et al. | 200/85 R |
| 1,500,057 | 7/1924 | Corns | 240/4 |
| 2,298,870 | 10/1942 | Cooper | 240/4 |
| 2,910,680 | 10/1959 | McLain | 340/311 |
| 3,584,169 | 6/1971 | Leu | 200/85 R |
| 3,781,843 | 12/1973 | Harrison et al. | 340/279 |

*Primary Examiner*—Glen R. Swann, III
*Attorney, Agent, or Firm*—Kirschstein, Kirschstein, Ottinger, Frank & Cobrin

[57] ABSTRACT

An alarm system for an invalid in a hopsital bed includes electric switches placed on top of the side rails and foot rail so that a force applied to any of said switches by a patient results in activation of a warning device. In addition, means is provided for selectively illuminating the hospital bed. Two basic configurations of electric switches are provided, both of which are characterized by the provision of a first switch member which is actuated by light pressure or force, and a second switch member which is actuated by heavier pressure, e.g. when the patient attempts to climb or crawl out of the bed, which could result in injury to the patient due to a fall from the bed to the floor. The switch members when actuated serve to close electric circuits which may sound a buzzer, and/or a call bell, and/or illuminate the bed, so that a nurse or attendant is amply alerted to give attention to the patient.

15 Claims, 24 Drawing Figures

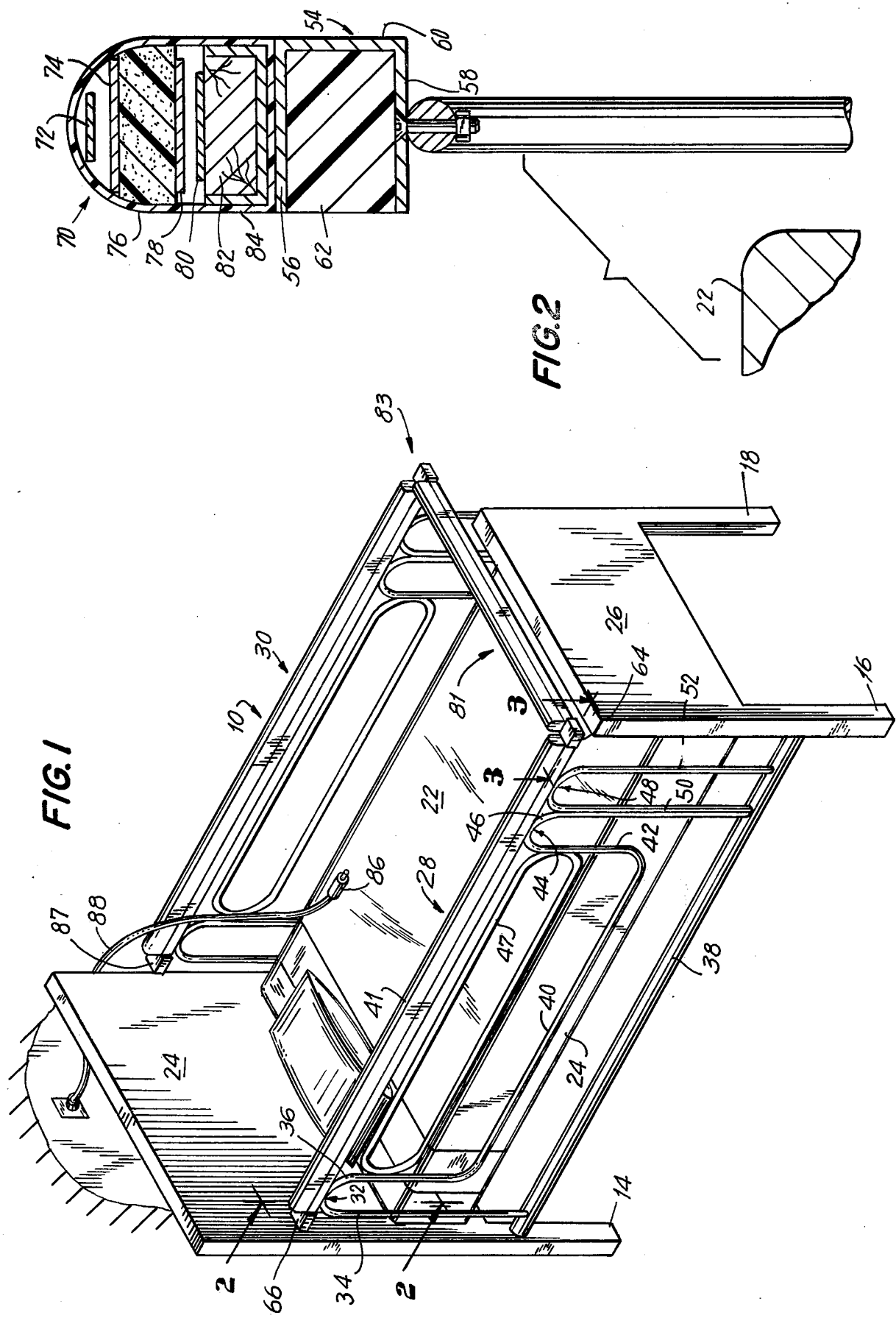

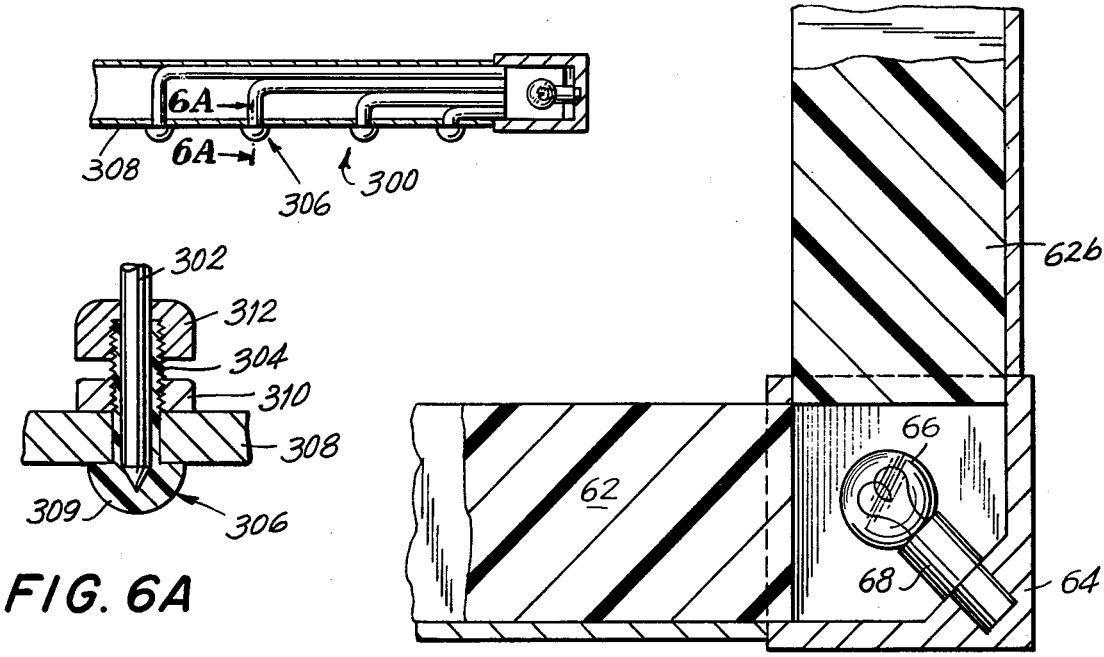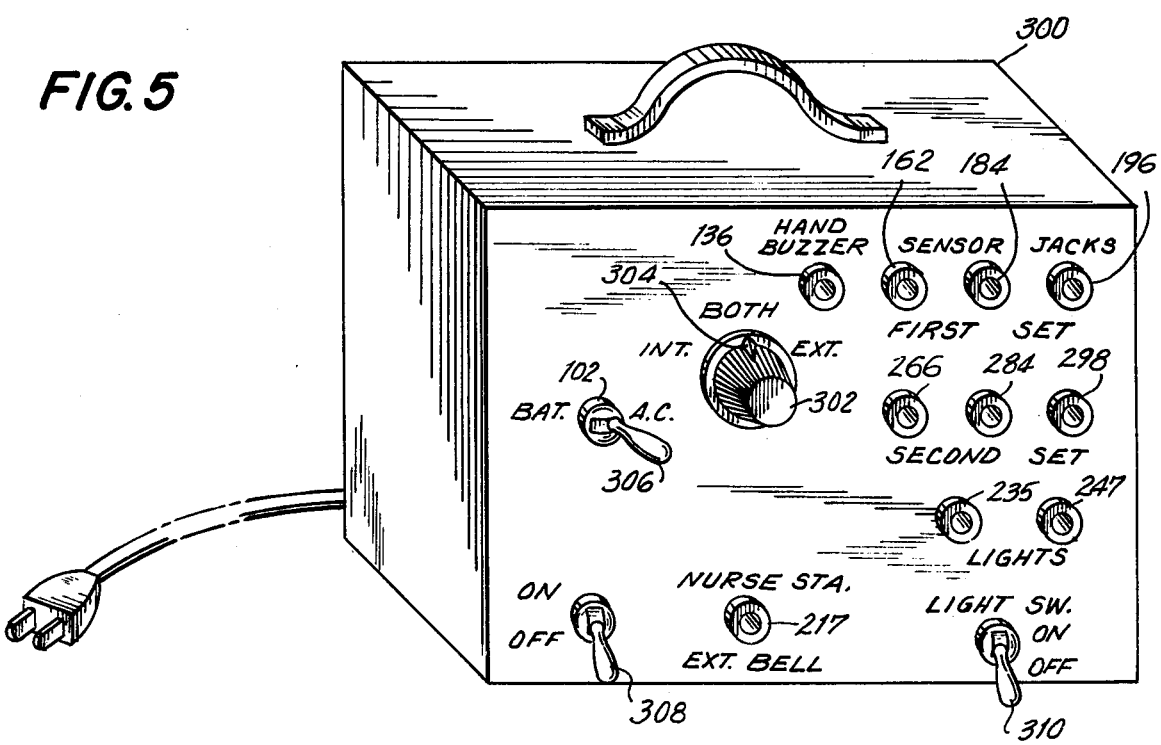

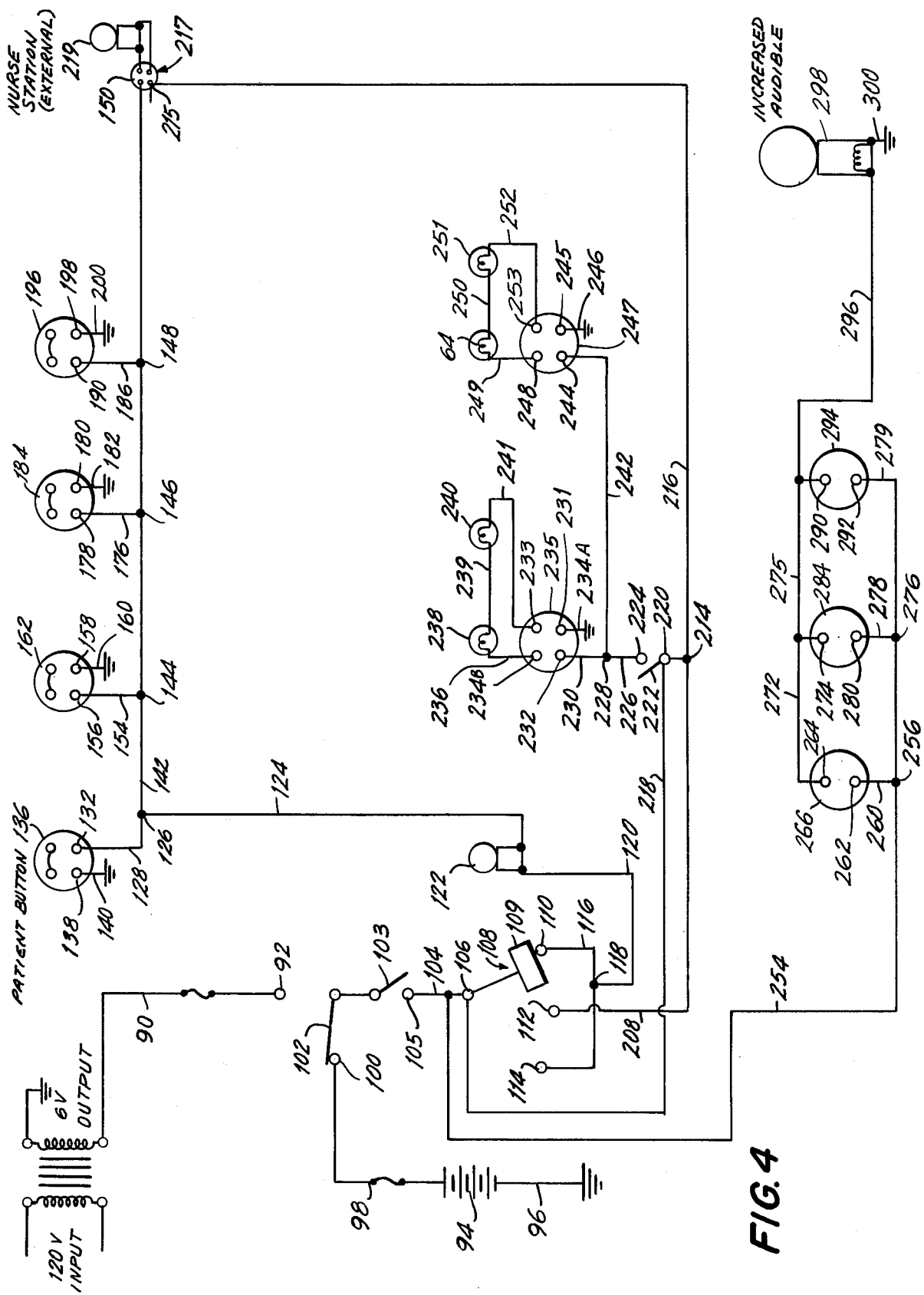

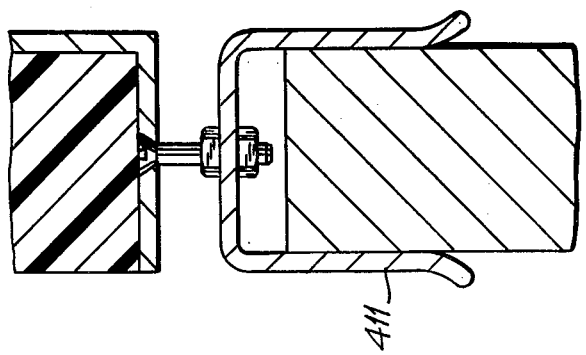
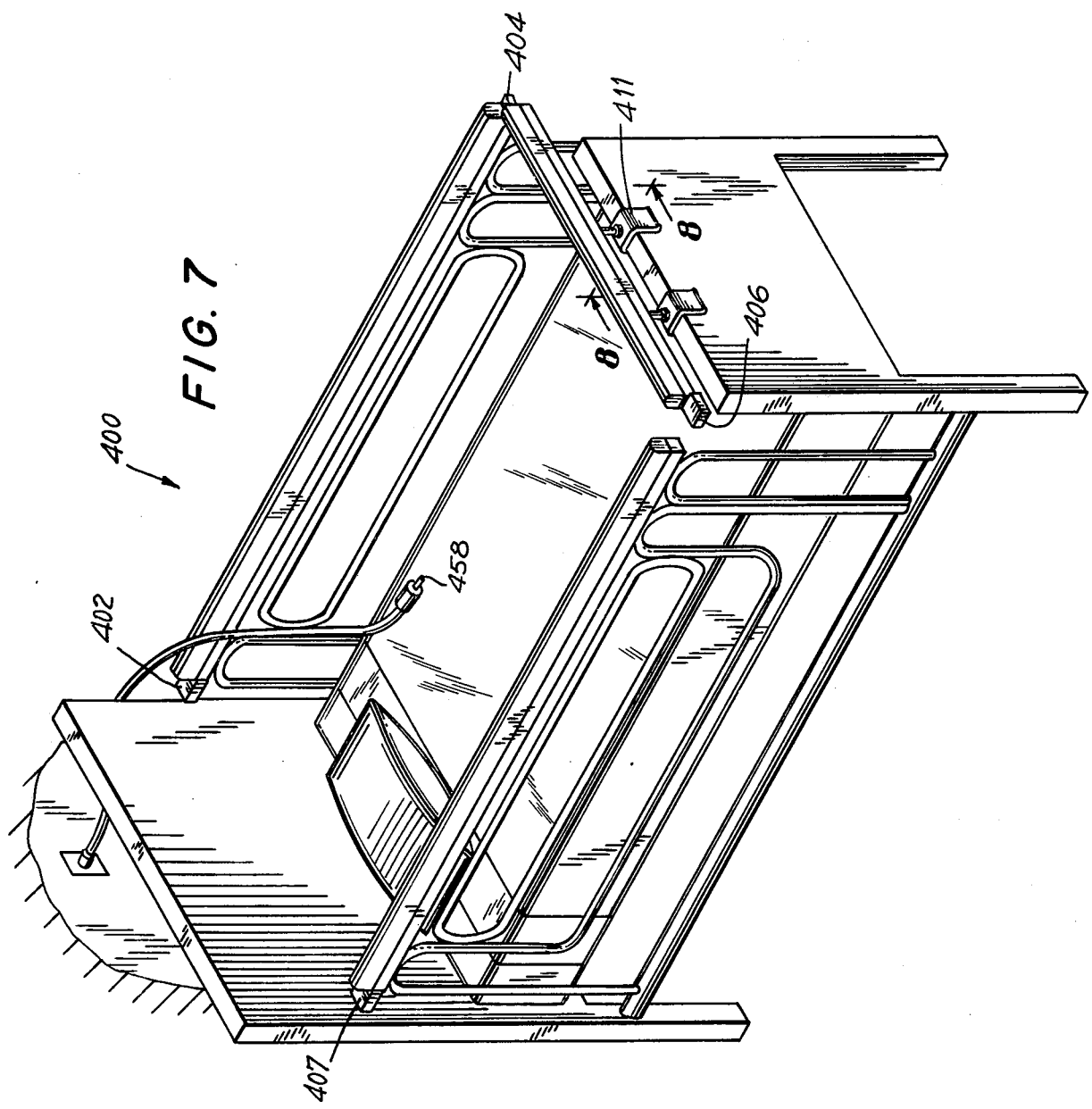

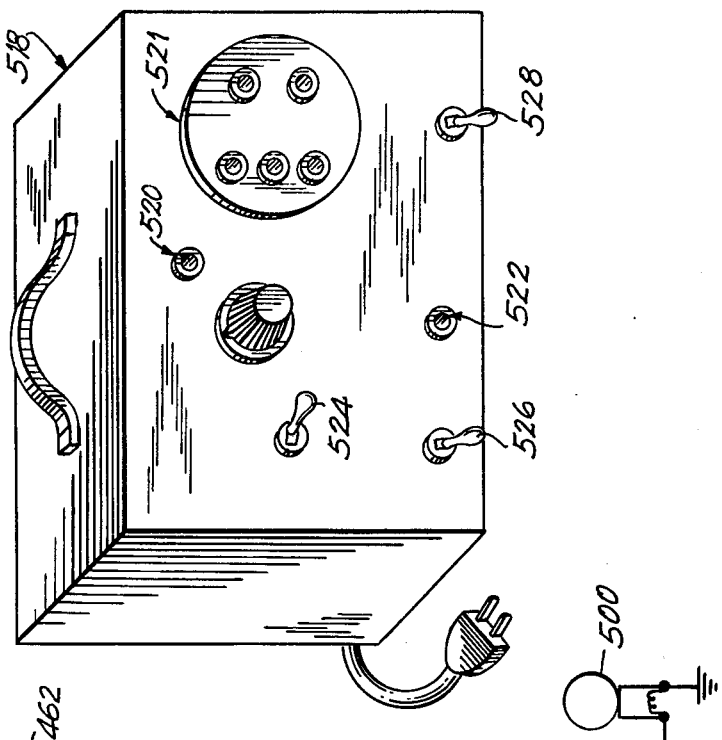
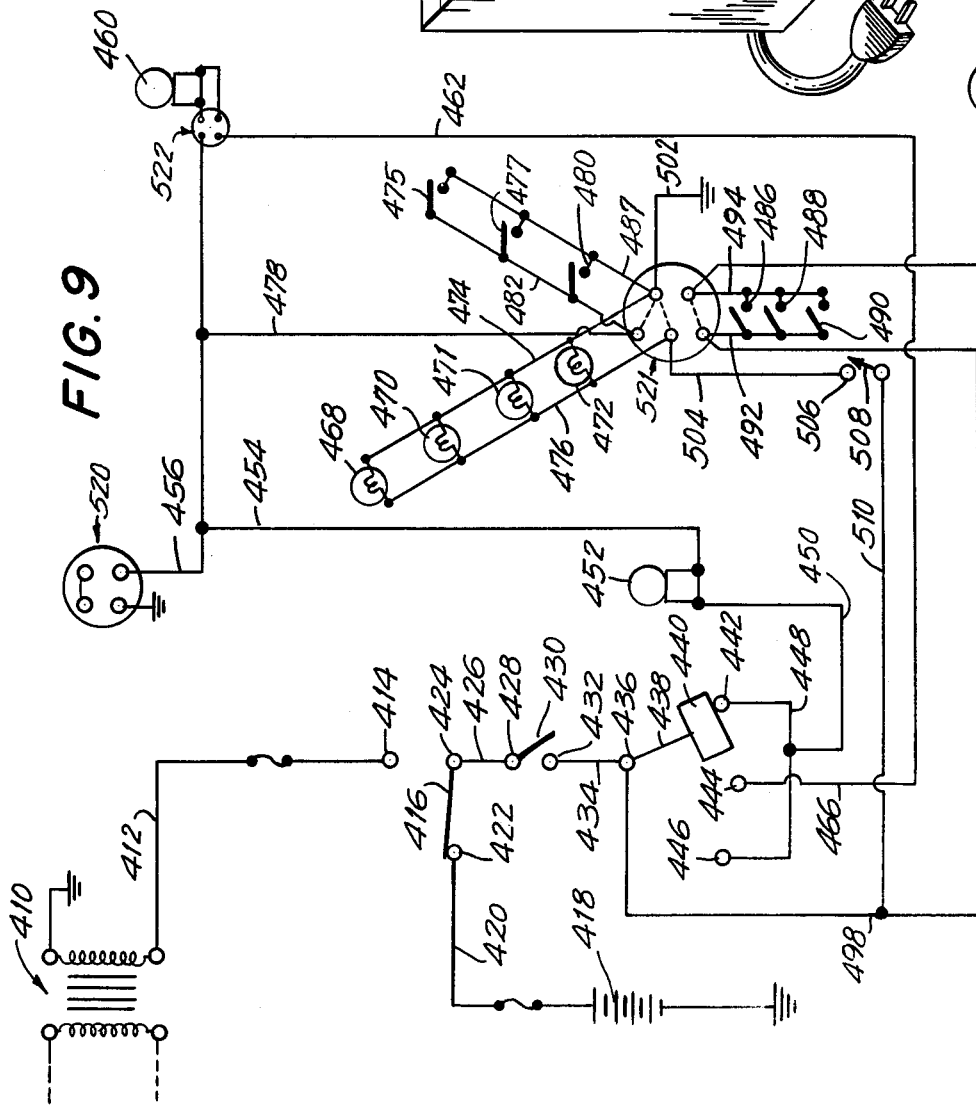

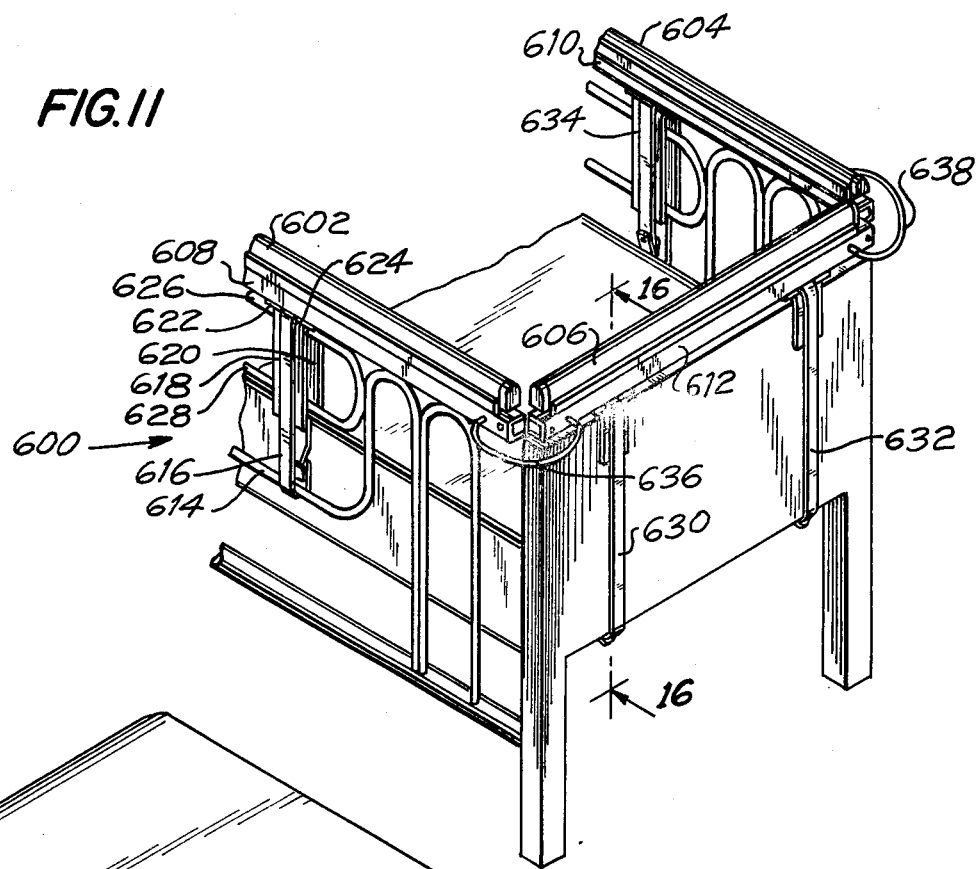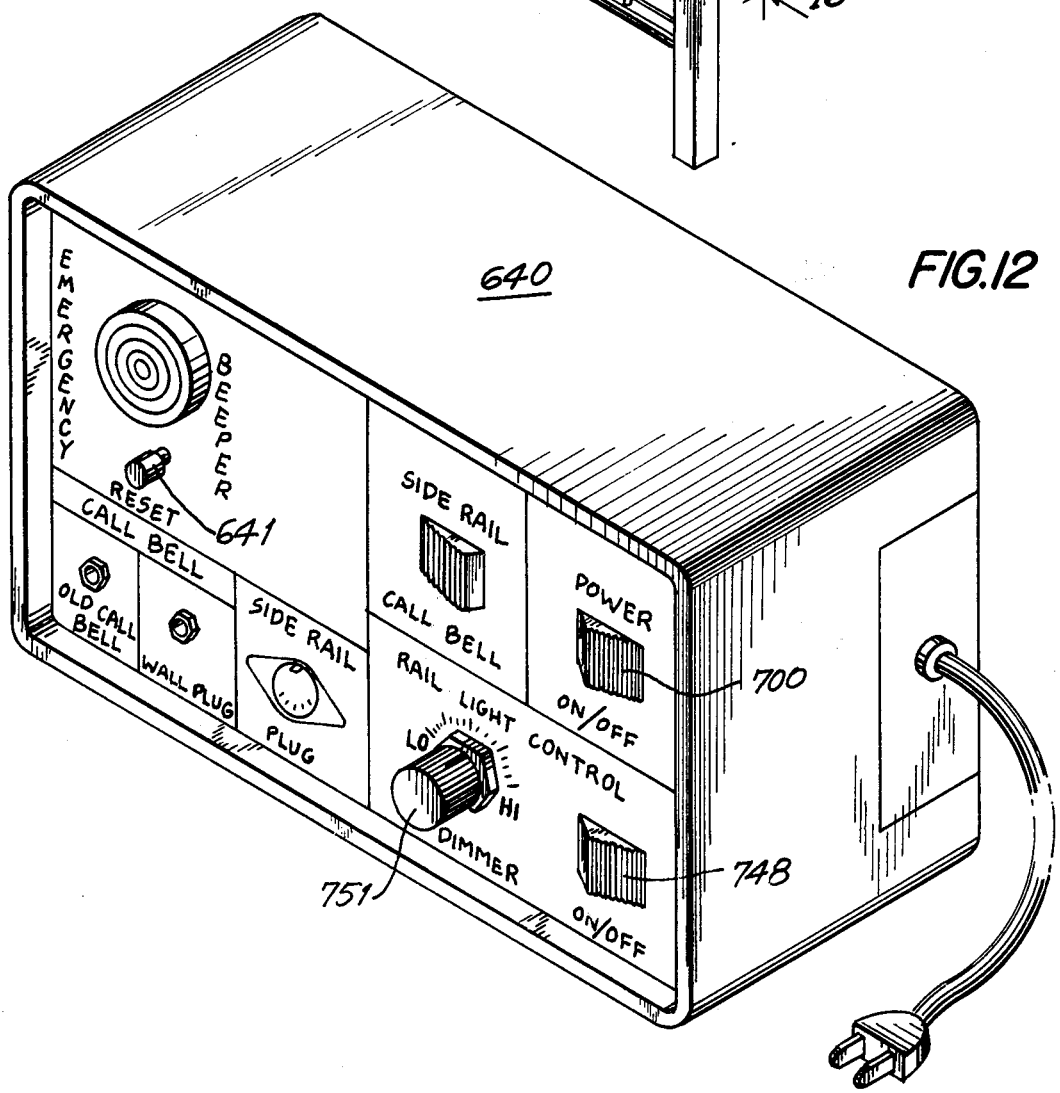

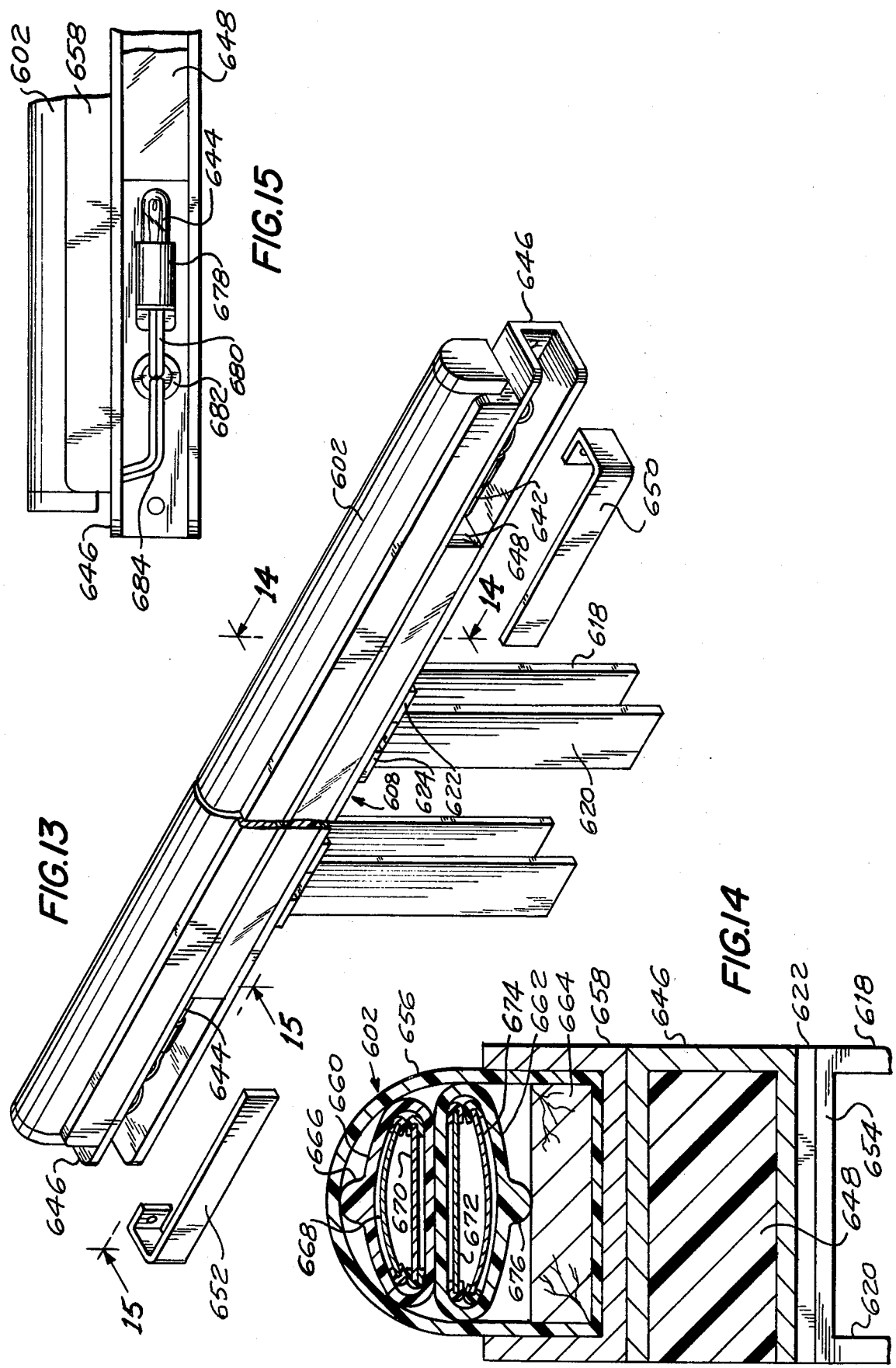

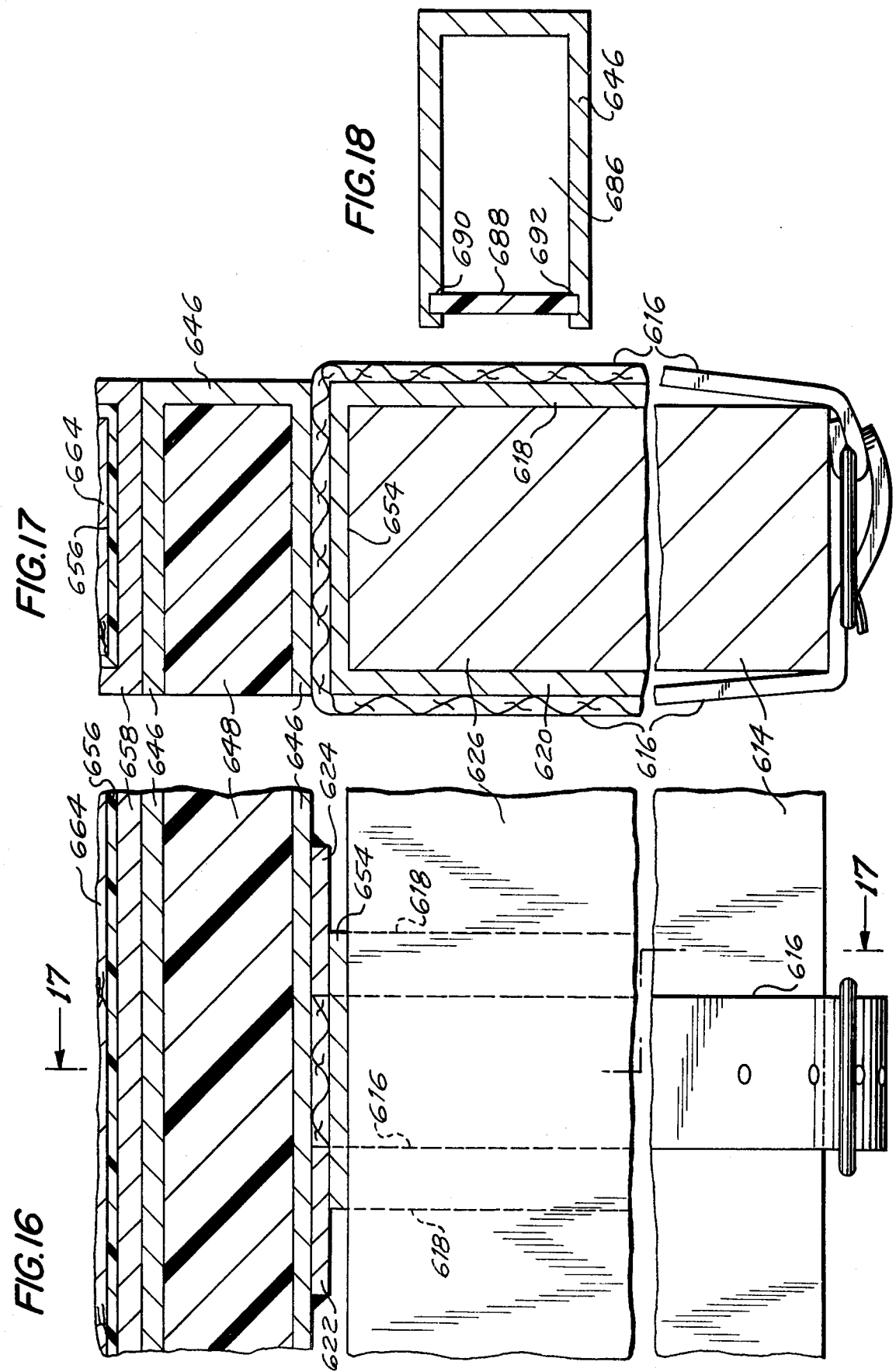

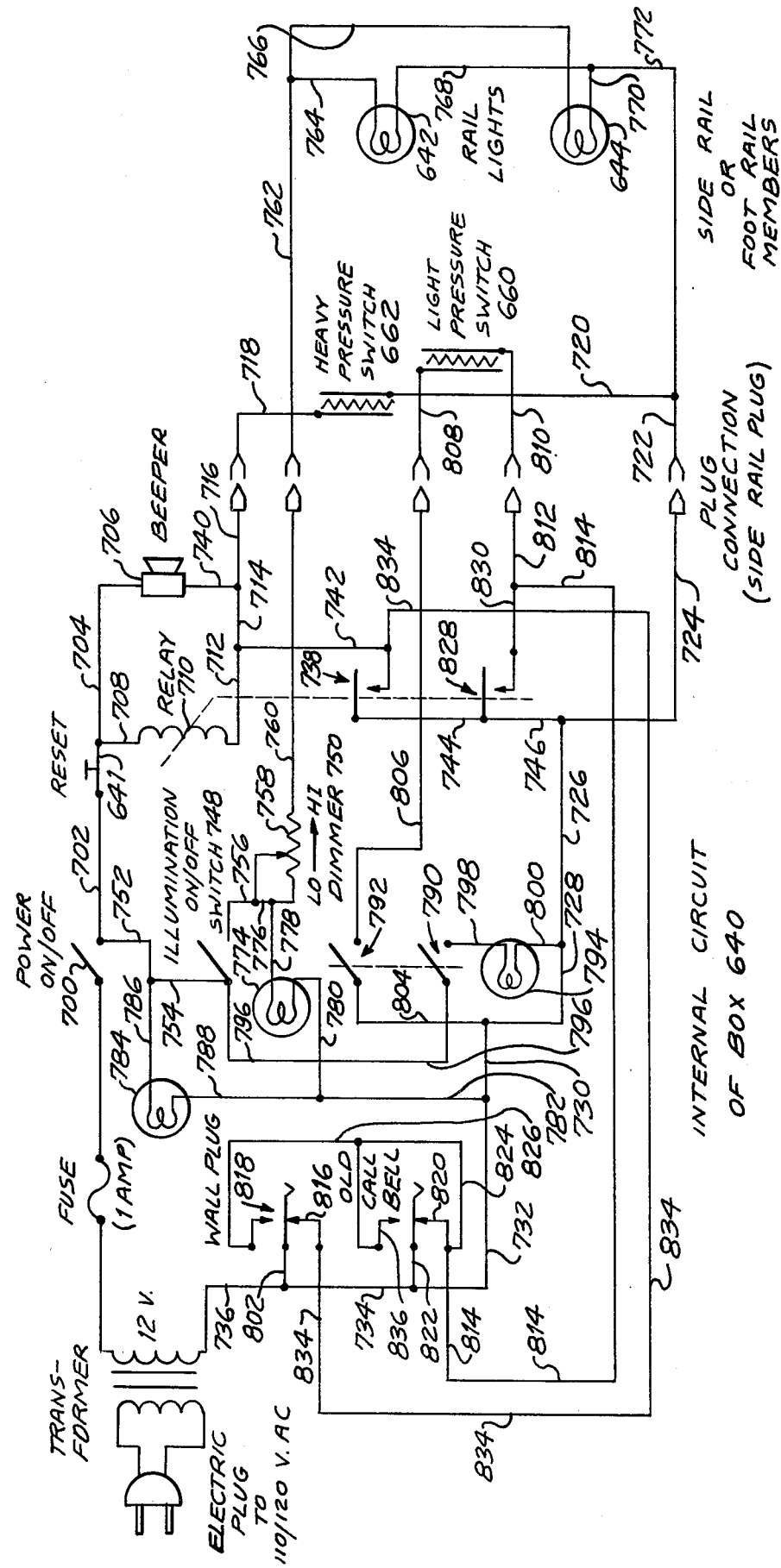

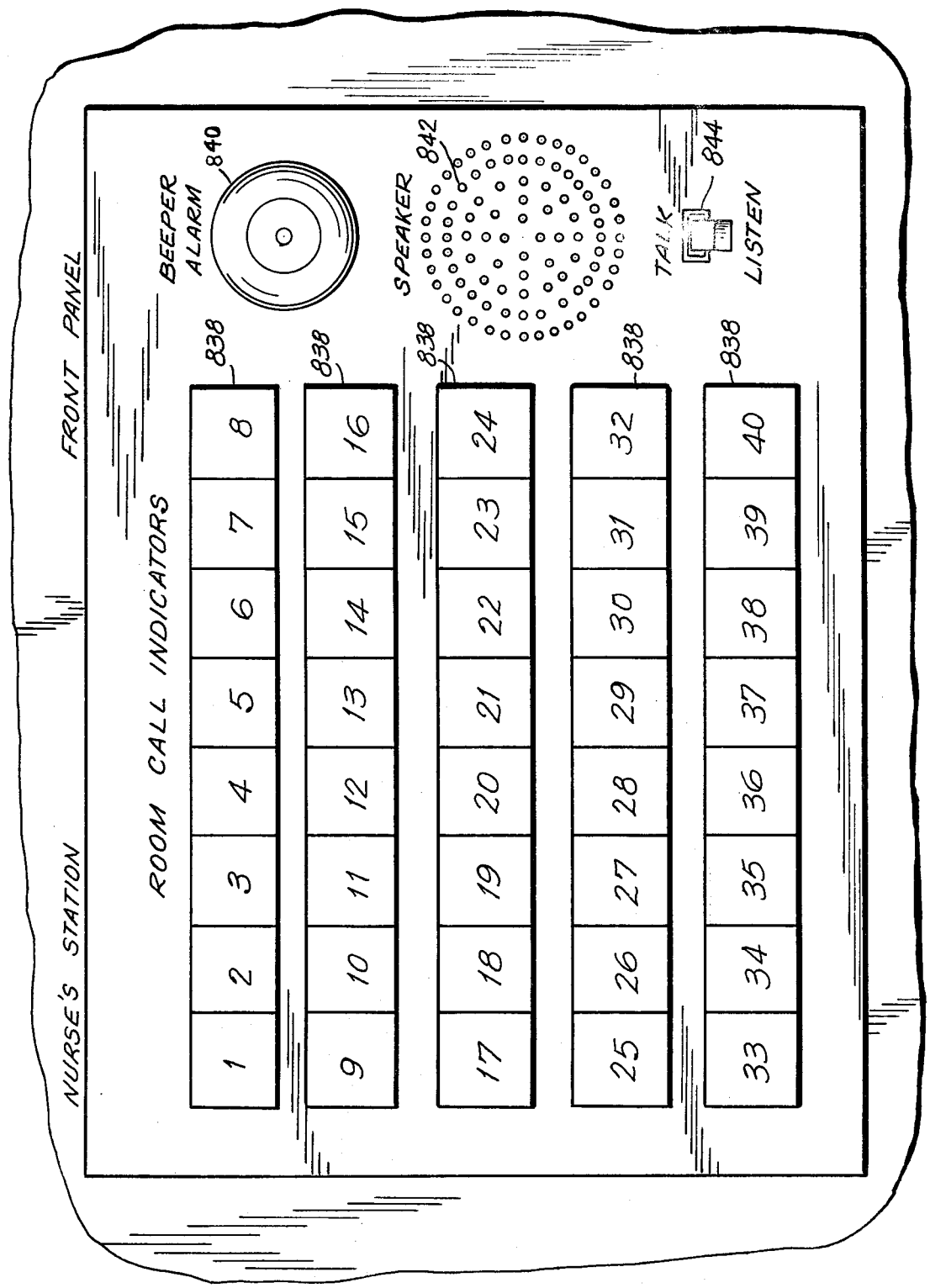

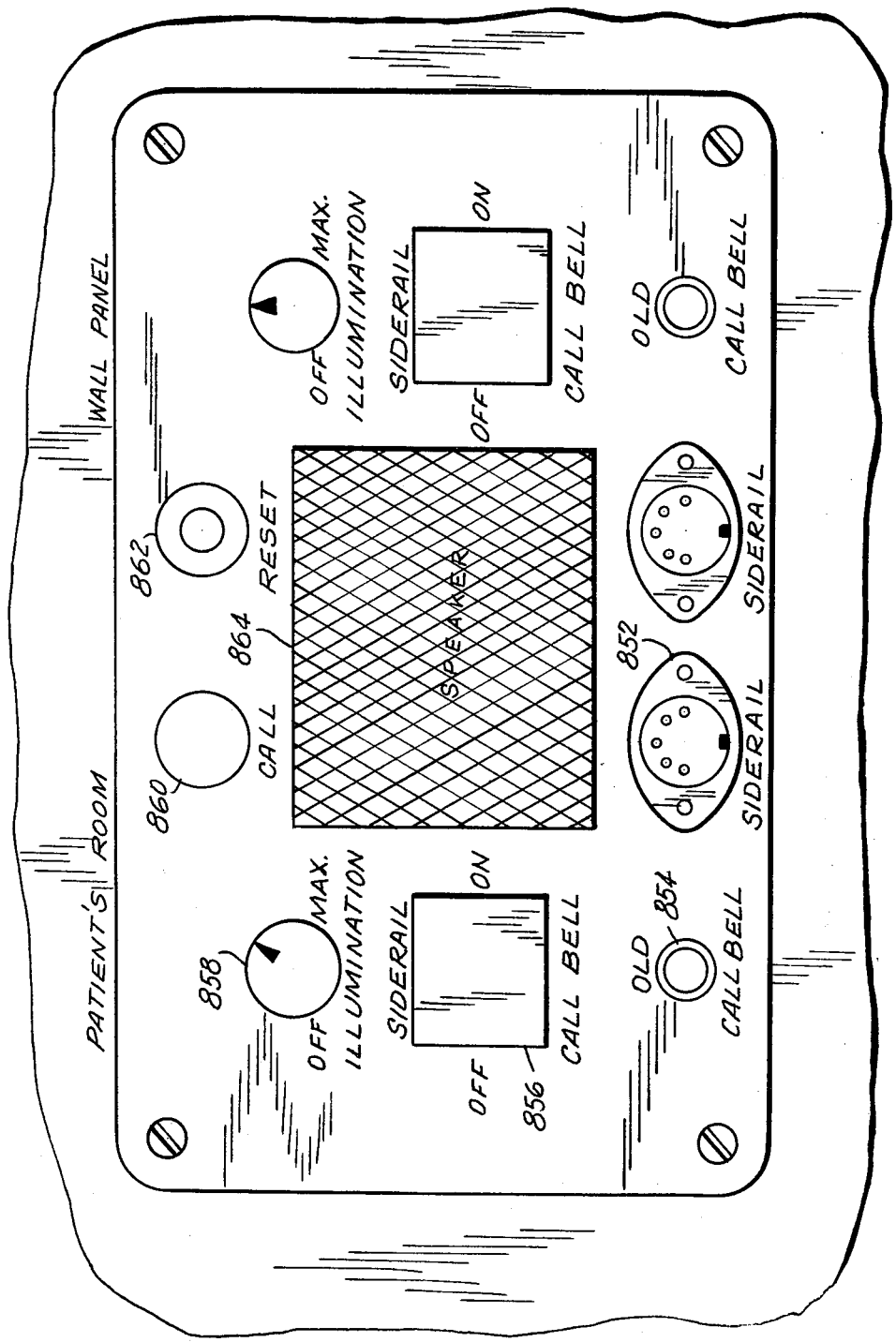

INVALID BED SYSTEM

CROSS-REFERENCE TO RELATED APPLICATION

The present application is a continuation-in-part of application Ser. No. 572,720 filed Apr. 29, 1975, now abandoned.

BACKGROUND OF THE INVENTION

1. Field of the Invention

Bed alarm system.

2. Description of the Prior Art

Elderly people and even younger people when bedridden and not in full possession of their mental faculties frequently fall out of bed with consequent harm to themselves. Efforts have been made to prevent this which efforts have included the placing of side rails at each side of the bed. Means have been provided for enabling the side rails to be raised or lowered. However, it has been found that patients frequently crawl over the side rails even when the side rails are elevated so that the fall is from an even greater height and the harm to the patient greater. In addition, many patients crawl over the foot rail at the foot of the bed which is normally not very high. Still further, there is a gap between the side rails and the foot rail through which patients have in the past crawled in an attempt to leave the bed with the result that the patients have fallen from the bed and hurt themselves.

It is desirable for a warning device to be activated advising when a bedridden patient is attempting to leave a bed so that the patient can be aided in these attempts without injuring himself. Still further, it is desirable that the patient be able to summon aid as needed. In the past a switch button has been provided for the patient which was connected to the nurses' station. When the patient desired a nurse's assistance he would activate the switch enabling a circuit to be completed so that a warning device (light and/or buzzer) would be activated at the nurses' station informing the nurse that the patient required assistance. The use of a patient actuated switch button for summoning assistance such as a nurse is usually satisfactory except that there are certain instances wherein a patient due to an enfeebled condition cannot find the switch button to call the nurse. This can present serious problems if the patient requires immediate attention and such attention cannot be given to the patient solely because a nurse is not aware of the patient's need for assistance.

It is often desirable to have a certain minimum amount of illumination during the evening hours for the bed in which an elderly bedridden patient sleeps.

SUMMARY OF THE INVENTION

1. Purposes of the Invention

It is an object of the present invention to provide an improved bed warning system.

Still another object of the present invention is to provide an improved bed warning system wherein a warning device is activated if an invalid tries to crawl out of the bed.

A further object of the present invention is to provide an improved bed warning system wherein a warning device can be activated as required in the room where the bed is and/or at a nursing station.

Yet a further object of the present invention is to provide an improved bed warning system which includes means for enabling a bedridden invalid to call for assistance wherein said means is readily locatable.

Yet a further object of the present invention is to provide an improved hospital bed wherein means is provided for preventing an invalid from crawling out of the bed and causing himself harm.

Still another object of the present invention is to provide an improved bed warning system wherein the system includes means for illuminating the bed.

Other objects of the invention in part will be obvious and in part will be pointed out hereinafter.

2. Brief Description of the Invention

The foregoing as well as other objects are accomplished in one embodiment of the invention by placing on the top of the side rails and foot of a hospital bed a tape switch. The tape switch is a switch whose switching conditions are changed upon sensing a weight. The tape switch is connected to a circuit which includes a source of power.

If the tape switch is activated by a patient applying a light pressure thereto a buzzer is activated in the patient's room and/or at a nursing station. This serves as a means of the patient indicating that he desires attention.

If heavy pressure is applied to the tape switch as when the patient is climbing out of bed a different buzzer is activated indicating that the patient must be given immediate attention so he will not injure himself as by falling from the bed.

Still further in another embodiment of the present invention means is provided for illuminating the hospital bed.

The invention accordingly consists in the features of construction, combination of elements and arrangement of parts which will be exemplified in the device hereinafter described and of which the scope of application will be indicated in the appended claims.

BRIEF DESCRIPTION OF THE DRAWINGS

In the drawings wherein like parts in the different Figures are identified by the same reference numeral:

FIG. 1 is a perspective view of a hospital bed according to the present invention;

FIG. 2 is an enlarged sectional view taken substantially along the line 2—2 of FIG. 1;

FIG. 3 is an enlarged sectional view taken substantially along the line 3—3 of FIG. 1;

FIG. 4 is a schematic illustration of a circuit of the present invention;

FIG. 5 is a perspective view of the box that is utilized in the present invention;

FIG. 6 is a partial sectional view of an alternate embodiment of the present invention;

FIG. 6a is an enlarged sectional view taken along the line 6a—6a of FIG. 6;

FIG. 7 is a perspective view of an alternate embodiment of the present invention;

FIG. 8 is a sectional view taken along the line 8—8 of FIG. 7;

FIG. 9 is a schematic illustration of a circuit for an alternate embodiment of the present invention;

FIG. 10 is a box for the alternate embodiment of the present invention;

FIG. 11 is a perspective view of a portion of an alternative hospital bed according to the present invention;

FIG. 12 is a perspective view of an alternative box that is utilized in the present invention;

FIG. 13 is a perspective view of an alternative electric switch assembly of the present invention;

FIG. 14 is a sectional elevation view of the switch of FIG. 13, taken substantially along the lines 14—14;

FIG. 15 is another sectional elevation view of the switch of FIG. 13, taken substantially along the lines 15—15;

FIG. 16 is an elevation view of a portion of the bed of FIG. 11, taken substantially along the lines 16—16;

FIG. 17 is a sectional elevation view of the bed portion of FIG. 16, taken substantially along the lines 17—17;

FIG. 18 is a cross-sectional view of an alternative arrangement for illuminating the bed;

FIG. 19 is a schematic illustration of an alternative circuit of the present invention;

FIG. 20 shows a wall panel at the nurse's station;

FIG. 21 shows a wall panel in the patient's room;

DESCRIPTION OF THE PREFERRED EMBODIMENTS

Figure 22:
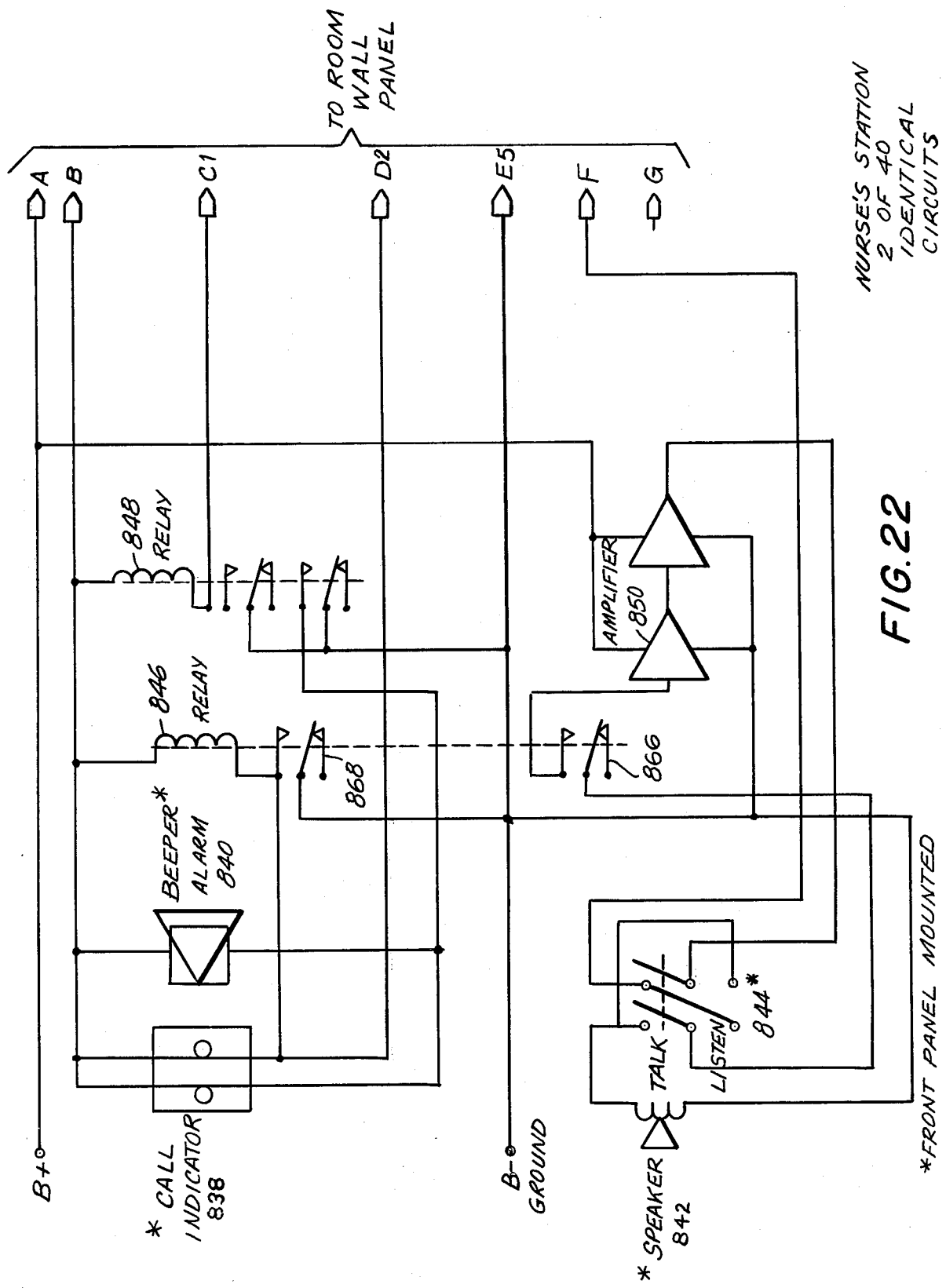
FIG. 22 is a wiring diagram relative to the nurse's control center at the nurse's station of FIG. 20.

In the drawings of hospital bed 10 according to the present invention is shown which includes legs 14, 16, 18 and a fourth leg which is not shown in the drawings. Hospital bed 10 also includes a mattress 22, a headboard 24 and a baseboard 26. Side rails 28 and 30 are provided.

An inverted U-shaped member 32 is provided which includes legs 34 and 36. Leg 34 at its bottommost portion is secured to a rod 38 which extends between hospital bed legs 14 and 16. Leg 36 extends to and is integral with a transverse section 40 which is horizontal. Transverse section 40 extends to a vertical leg 42 which is part of a U-shaped member 44 having a second leg 46. Leg 46 extends to and is attached to rod 38. Legs 42 and 36 are secured to elliptical rail member 47.

An inverted U-shaped member 48 includes legs 50 and 52 with leg 50 being secured to leg 46. In addition, legs 50 and 52 at their bottommost portion are secured to rod 38. The uppermost portion of inverted U-shaped member 48 prevents a patient from crawling through the space between leg 46 and baseboard 26, which space was heretofore sometimes open and presented an unimpeded path for a patient to crawl from a hospital bed. Identical structure is on the opposite side of the bed.

In FIG. 2 a casing 54 is shown which extends for the length of side rail 28 and includes a top 56, a bottom 58 and a vertical portion 60. Casing 54 is secured by screws (one of which is shown in FIG. 2) to the upper portions of U-shaped members 32, 44 and 48. Alternatively, a clamp may be used. It is to be appreciated that the inside surface of vertical section 54 faces away from the hospital bed.

A fibre optic rod 62 extends between 56, 58 and 60 for the length of side rail 28. At one end fibre optic rod 62 extends to and slightly into a light box 64 (FIG. 3). Light box 64 is rectangular in plan and casing 54 is secured thereto. Located in light box 64 and at a forty-five degree angle to the longitudinal axis of fibre optic rod 62 is a bulb 66 which is secured by a socket 68. The remaining end of fibre optic rod 62 is secured and extends to a light box 66 which is identical to light box 64 except that only one fibre optic rod extends to light box 66 as will be more particularly pointed out hereinafter. Casing 54 is secured to light box 66.

Located on casing top 56 is a tape switch 70. Tape switch 70 includes normally parallel metal contacts 72 and 74 at the uppermost portion thereof. Metal contact 74 rests on a resilient material which can be of polyfoam construction and which is identified herein by reference numeral 76. Located beneath resilient material 76 is a metal contact 78 and directly therebeneath is a further metal contact 80. Metal contact 80 rests on a wooden block 82 which is incompressible. A plastic sheath casing 84 surrounds the aforesaid tape switch structure. Identical tape and fibre optic structure is provided on rail 30. The tape and fibre optic structure on rail 30 is identified in the specification by the same reference numerals that are used in the drawings on the tape and fibre optic structure for rail 28 only followed by the suffix "A". In a similar fashion, identical switch and fibre optic structure is provided above the baseboard 26. The tape and fibre optic structure above baseboard 26 are not shown but are identified in the specification by the same reference numerals used in the drawings on the tape and fibre optic structure for rail 28 only followed by the suffix "B".

Fibre optic 62B extends to light box 64 and light box 83. Each fibre optic rod is joined to a light box as heretofore explained. Fibre optic 62 extends to light box 66 as well as to light box 64. Casing 54A extends to and is secured to light boxes 88 and 83, whereas, casing 54B extends to and is secured to light boxes 83 and 64.

As is conventional a patient is provided with an alarm button 86 which is connected to a wire 88. The circuit for the present invention is shown in FIG. 4 and is hereinafter described.

A line 90 is connected to a transformer at one end and to a terminal 92. A battery 94 is grounded at one end by a wire 96 and is connected at the other end by a wire to a terminal 100. A switch lever 102 is provided and can be selectively placed in contact with either terminal 92 or 100. When it is desired to use the battery and not an external source of voltage, lever 102 is brought in contact with terminal 100. Lever 102 is connected to switch lever 103 which is a power-on power-off switch lever and cooperates with terminal 105. Terminal 105 is connected to a terminal 106 and a rotary switch 108. Rotary switch 108 includes terminals 110, 112 and 114 of a bridge 109. A wire 116 is connected to terminals 110 and 114 and to a further terminal 118. Wire 120 connects terminal 118 to buzzer 122.

Buzzer 122 is located adjacent bed 10. The remaining terminal of buzzer 122 is connected via a wire 124 to a terminal 126.

Terminal 126 is connected via wire 128 to a terminal 132. Terminal 138 via wire 140 is connected to ground. A socket 136 is provided which includes terminals 132 and 138. A jack connected to the patient button is adapted to be placed in socket 136. Upon the patient button being depressed, terminals 132 and 138 are placed in circuit with each other. At all other times, terminals 132 and 138 are not in circuit with each other. A wire 142 is connected to terminal 126 and to terminals 144, 146, 148 and to a terminal 150.

A wire 154 is connected to terminal 144 and to a terminal 156. Terminal 158 is connected by wire 160 to ground. Terminals 156 and 158 are part of a socket 162 which is connected to contacts 72 and 74 of the casing structure of the side rail 28. Upon contacts 72 and 74 being in circuit with each other, terminals 156 and 158 are in circuit with each other. At all other times, terminals 156 and 158 are electrically isolated from each other.

A wire 176 is connected to terminal 146 and to terminal 178. A terminal 180 is connected by wire 182 to ground. Terminals 178 and 180 are part of socket 184 and a jack connected to the contacts 72A and 74A is connected to socket 184. When contacts 72A and 74A touch each other terminals 178 and 180 are in circuit with each other. At all other times, terminals 178 and 180 are electrically isolated from each other.

A wire 186 is connected to terminal 148 and to terminal 190. A wire 200 is connected to terminal 198 and to ground. Terminals 190 and 198 are part of socket 196. A jack which is connected to contacts 72B and 74B is also connected to socket 196. Terminals 190 and 198 are in circuit with each other only when contacts 72B and 74B touch.

A wire 208 is connected to terminals 112 and 214. A wire 216 is connected to terminal 214 and to terminal 215. Terminals 150 and 215 are part of socket 217. A jack which is connected to buzzer 219 is inserted into socket 217. Buzzer 219 is located at the nurses' station which, as the case may be, is either in close proximity to the patient's room or a reasonable distance therefrom.

A wire 218 is connected to terminal 220 and to terminal 106. A switch lever 222 is connected to terminal 220 and can be selectively placed in circuit with terminal 224. A wire 226 connects terminal 224 to terminal 228. A wire 230 connects terminal 228 to terminal 232. A terminal 231 is connected by wire 234A to ground. Terminals 232 and 231 are part of socket 235. A terminal 234B is connected by wire 236 to bulb 238. A wire 239 connects bulb 238 to bulb 240. A wire 241 connects bulb 240 to terminal 233. Terminals 234B and 233 are connected by a jack placed in socket 235 to terminals 232 and 231, respectively.

A wire 242 connects terminal 228 to terminal 244. A terminal 245 is connected by wire 246 to ground. Terminals 244 and 245 are part of socket 247. A terminal 248 is connected by wire 249 to bulb 64. Bulb 64 is connected by wire 250 to bulb 251. Bulb 251 is connected by wire 252 to terminal 253. Terminals 248 and 253 are connected to a jack which is inserted into socket 247. Bulbs 238 and 240 are located in boxes 83 and 87 whereas bulbs 251 and 64 are located in boxes 64 and 66.

A wire 254 is connected to terminal 105 and to terminal 256. A wire 260 is connected to terminal 256 and to terminal 262. A terminal 264 is provided and terminals 262 and 264 are part of socket 266. A jack which is connected to contacts 78 and 80 is inserted in socket 266 and when contacts 78 and 80 are in circuit with each other terminals 264 and 262 are in circuit with each other. At all other times terminals 262 and 264 are electrically isolated from each other.

A wire 272 is connected to terminal 264 and to terminal 274. It is to be appreciated that wire 254 is connected to terminals 276 and 292 as well as terminal 256. A wire 278 is connected to terminal 276 and to terminal 280. Terminal 280 and terminal 274 are part of socket 284. A jack which is connected to the contacts 78A and 80A is inserted in socket 284. Upon the contacts 78A and 80A being in circuit with each other terminals 280 and 274 are in circuit with each other. At all other times terminals 280 and 274 are electrically isolated from each other.

A wire 275 connects terminal 274 to terminal 290. A wire 279 connects terminal 276 to terminal 292. Terminals 290 and 292 are part of socket 294. A jack which is connected to contacts 78B and 80B is inserted into socket 294. When contacts 78B and 80B touch each other terminals 290 and 292 are in circuit with each other and at all other times terminals 290 and 292 are electrically isolated from each other.

A wire 296 connects terminal 290 to a buzzer 298 which is located in the patient's room. A wire 300 grounds buzzer 298. Buzzer 298 has a different pitch than buzzer 122 for a reason that will soon be apparent.

If it is desired to have bulbs 238, 240, 251 and 64 illuminated, such as during the evening hours so that the patient and the rail structure will be readily visible, switch levers 103 and 222 are closed. Terminals 220 and 224 are now in circuit with each other and are connected to the source of power. electrical energy will be directed to each of the bulbs and to the fibre optic rods adjacent each bulb so that the bed will be illuminated for the benefit of the patient as well as for the benefit of anybody who wishes to observe the patient without disturbing the patient.

If it is desired to have the alarm system set so that if the patient calls the nurse only the buzzer (122) inside the patient' room is activated, the rotary switch is positioned so that contact bridge 109 spans terminal 110 only. With bridge 109 contacting terminal 110 electrical potential is directed to buzzer 122; however, the buzzer is inactive since it is not grounded. If a patient should decide to activate the buzzer inside his room (122) to call for a nurse button 86 is depressed placing terminals 132 and 138 in circuit with each other. Buzzer 122 is now grounded via wire 124, terminal 126, wire 128, terminals 132 and 138 and wire 140 and the buzzer 122 is activated. Similarly, the patient can activate buzzer 122 by manually applying a light pressure (e.g., a pound and one-half) on top of any of the side rails or on top of the rail above the baseboard to bring any of contacts 72 and 74 in abutment with each other. Heavy pressure (about twenty pounds) is required to cause contacts 78 and 80 to touch. As an example, a patient, by placing his hand on plastic sheath 84 and applying a light pressure, causes contacts 72 and 74 to touch placing terminals 158 and 156 in circuit with each other grounding buzzer 122 and resulting in activation of said buzzer. In a similar fashion, the tape switches above the remaining side rail and above the baseboard can be activated.

If it is desired to inactivate buzzer 122 so only buzzer 219 at the nurses' station is activated, bridge 109 is placed in contact with terminal 112 alone. In this condition of the rotary switch electrical energy is directed to buzzer 219 via terminal 112 and wire 216. However, buzzer 219 is not activated inasmuch as it is not grounded. Depression of button 86 places terminals 132 and 138 in circuit with each other grounding buzzer 219 and resulting in activation of the same. Normally a light which has indicia associated with the patient's room will be illuminated when buzzer 219 is activated so that the nurse will know which room requires attention. In a similar fashion, if the patient places his hand on any of the tape switches with the sufficient pressure to cause any of the contacts 72 and 74 to touch each other buzzer 219 is activated. Buzzer 122 is never activated with bridge 109 in contact with terminal 112 alone.

If it is desired that both buzzer 219 and 122 be activated upon the patient placing a light pressure on a tape switch or depressing button 86, then bridge 109 is positioned so as to span terminals 112 and 114. In this condition if button 86 is depressed placing terminals 132 and 138 in circuit with each other both buzzers 122 and 219 are grounded and activated. In a similar fashion if the patient places enough pressure to close a pair of the light pressure contacts both buzzers 122 and 219 are grounded.

The system provides an indication of when the patient is trying to climb out of bed irrespective of the position of bridge 109. If a patient is trying to climb out of bed over rail 28 a sufficient force will be applied to a tape switch so that contacts 78 and 80 touch each other and terminals 262 and 264 are in circuit with each other. Consequently, electrical potential from wire 254, terminal 256, wire 260, terminal 262, terminal 264, wire 272, wire 275 and wire 296 is directed to buzzer 298 which is activated. Normally, this buzzer will be sufficiently loud so as to alert people in the immediate vicinity of the patient's room that the patient is trying to climb out of bed so that immediate attention can be given to the patient to prevent him from harming himself, such as by falling from the bed.

It is, of course, to be appreciated that when the heavy pressure contacts 78 and 80 touch each other the light pressure contacts 72 and 74 touch each other and if bridge 109 is contacting terminal 114, as well as terminal 112, buzzer 122 inside the patient's room and buzzer 219 at the nurses' station will be activated. However, normally a nurse will not immediately respond tp activation of buzzer 219 but activation of buzzer 298 will bring immediate attention to the patient since this indicates that the patient may be in a dangerous situation as from trying to climb out of the bed. The nursing staff should be trained so that upon hearing buzzer 298 immediate attention is directed to the patient.

The circuit, buzzer 122 and buzzer 298 can be provided in a box 300 such as shown in FIG. 5. By utilizing box 300 which is placed in a patient's room, the advantages of the present invention can be derived in a simple manner. Knob 302 on box 300 controls the position of bridge 109. As an example, when blade 304 on knob 302 is beneath the word "BOTH" bridge 109 spans terminals 112 and 114 so that buzzer 122 inside the patient's room and buzzer 219 at the nurses' station will be activated. On the other hand, if knob 302 is rotated so that blade 304 is under "INT" (which is an abbreviation for internal) then bridge 109 contacts terminal 110 only so that only buzzer 122 is activated. If knob 302 is totated so that blade 304 is under the abbreviation "EXT" (which abbreviation stands for external meaning that the buzzer at the nurses' station alone would be activated) then bridge 109 contacts only terminal 114.

Normally, battery 94 will be located in box 300 and a plug will be provided. Toggle switch 306 when in the position shown in FIG. 5 adjacent the notation "A.C." places switch lever 102 in contact with terminal 92. On the other hand, when toggle lever 306 is adjacent the notation "BAT." (abbreviation for battery) lever 102 contacts terminal 100.

Toggle lever 308 when in the position shown in the drawings adjacent the word "OFF" causes switch lever 103 to be spaced from terminal 105 so that the system is inoperative. On the other hand, when toggle lever 308 is adjacent the word "ON" switch lever 103 contacts terminal 105 so that the system can operate.

Socket 217 is identified on box 300 by the notation "NURSES STA. EXT. BELL" which notation stands for nurses' station external bell. A toggle lever 310 under the notation "LIGHT S.W." (light switch) controls the position of lever 222. When toggle lever 310 is adjacent the word "OFF" switch lever 222 is spaced from terminal 224. On the other hand, when toggle lever 310 is adjacent the word "ON" switch lever 222 contacts terminals 224. Sockets 235 and 247 are shown on the face of box 300. In a similar fashion, sockets 162, 184 and 196 are shown on the face of box 300. Additionally, sockets 270, 284 and 294 are located on the face of box 300 as is socket 136.

It is to be appreciated that if desired heavy duty buzzer 298 could be located at the nurses' station instead of in the patient's room. This would enable a nurse at the nurses' station upon hearing activation of buzzer 298 to realize that immediate attention was required for the patient. On the other hand, if the nurse hears the activation of buzzer 219 she knows that while attention is required of the patient it is not necessarily urgent.

If desired, instead of using fibre optic rods as shown in the drawings and heretofore described, groups of fibre optic rods can extend from each light box to openings in closed rails along the side rails and foot rail. Each group of fibre optic rods will extend to an opening in a closed rail so that rather than a continuous beam of light there will be spaced apart pin points of light. This is shown in FIGS. 6 and 6a wherein a plurality of groups of fibre optic rods 300 extend from a light box to spaced openings on the exterior wall 308 of casing 54.

In FIG. 6a of the drawings, a fibre optic casing 302 extends through a threaded sleeve 304. Affixed to threaded sleeve 304 is a translucent plastic head member 306 which extends through an opening in wall 308 and includes a head 309.

A nut 310 is threaded about sleeve 304 and abuts the inside surface of wall 308. A nut 312 is screwed about sleeve 304.

In FIGS. 7, 8, 9 and 10 of the drawings, an alternate embodiment 400 of the invention is shown and is similar to the first embodiment with only the differences set forth herein. In the embodiment of the invention shown in FIGS. 7, 8, 9 and 10, light boxes 406 and 404 are affixed to the railing structure above the baseboard which railing structure is secured by clamps 411 to the baseboard. Light box 402 is secured to the rail structure above side rail 30 whereas light box 407 is secured by the side rail 28. Light box 406 is spaced from and adjacent to the fibre optic rod associated with side rail 28 which fibre optic rod does not extend into the light box. In this connection, light box 406 has a hole through which light is emitted to the fibre optic rod associated with said rail 28. Light box 404 similarly is spaced from the fibre optic rod associated with side rail 30. The fibre optic rod associated with the baseboard extends to light boxes 404 and 406. A patient call button 458 is provided.

In FIGS. 9 and 10, a transformer 410 is connected by wire 412 to a terminal 414. AC-DC lever 416 cooperates with terminals 414 and 422. A battery 418 is connected by wire 420 to terminal 422.

A wire 426 connects terminal 424 to terminal 428 and lever 430. Power switch lever 430 cooperates with terminal 432 which is connected by wire 434 to terminal 436. A wire 438 connects terminal 436 to bridge 440 which cooperates with terminals 442, 444 and 446 in the same manner that bridge 109 cooperates with terminals 100, 112 and 114.

A wire 448 is connected to terminals 442 and 446 and to wire 450 which is connected to room buzzer 452. A wire 454 is connected to wire 456 which leads to socket 520.

Patient call button 458 is connected to socket 520 as is wire 456 and upon being depressed grounds wire 456. Wire 456 is connected to socket 522 as is the nurses' station buzzer 460. Wire 462 is connected to socket 522 and via wire 466 to terminal 444.

Lights 468, 470, 471 and 472 are located in the respective light boxes and are attached to wires 474 and 476. Wire 478 is connected to wire 456.

The light pressure switches 475, 477 and 480 are connected to wires 482 and 487. The heavy pressure switches 486, 488 and 490 are connected to wires 492 and 494.

A wire 496 is connected to terminal 436 via wire 498 and to a first prong of a five-prong plug to which wire 492 is attached. A wire 498 is connected to a heavy duty buzzer 500 (within the patient's room) and to a second prong of the five-prong plug. Also connected to the second prong is wire 494. Connected to the third prong are wires 474 and 487 and a ground wire 502.

Connected to the fourth prong are wires 482 and 478 while connected to the fifth prong are wires 476 and 504. A five socket receptacle 521 is provided which receives the five prongs. Wire 504 is connected to terminal 506. Light switch lever 508 cooperates with terminal 506 and is connected to wire 496 by wire 510.

In FIG. 10 a box is shown which includes socket 520 which receives a jack leading to the patient call button. Socket 521 receives the five prongs. Socket 522 receives the jack leading to buzzer 460. Toggle switch 524 controls the position of lever 430, whereas toggle switch 526 controls the position of light switch lever 508. Toggle switch 528 controls the position of switch lever 416. Housed within the box is the circuit and the two buzzers in the patient's room as well as the battery.

The operation of the embodiment just described is the same as the operation of the previous embodiment except that the circuitry is greatly simplified.

Referring now to FIG. 11, a bed 600 is characterized by the provision of horizontal side rail switches 602 and 604 and foot rail switch 606, light transmission means 608 associated with the switch 602, light transmission means 610 associated with the switch 604, and light transmission means 612 associated with the switch 606. The elements 602 and 608 are attached to a lower horizontal side rail 614 by a plurality of vertically oriented straps such as a strap 616 which extends about vertical plates 618 and 620 which depend from and are attached to an upper horizontal member, not shown, which in turn is attached to spaced apart horizontal shims 622 and 624, the upper surfaces of which are attached to the lower surface of member 608. The shims 622 and 624 are spaced apart to accommodate the upper portion of the strap 616, so that this upper portion bears against the upper horizontal member between plates 618 and 620. In addition, vertical portions of strap 616 bear against the outer surfaces of members 618 and 620, so that the assemblage is firmly held in place on top of the side rail of the bed. The assemblage actually rests on upper horizontal rail 626.

It is to be noted that members 618 and 620 extend below middle horizontal side rail member 628, so that pivoted movement of the assemblage of elements 602 and 608 about a lower horizontal axis is effectively prevented. Similar restraining straps 630 and 632 are provided for the assemblage of the elements 606 and 612, and one of the restraining straps 634 for the assemblage of elements 604 and 610 is also shown. Electrical cord 636 having multiple wires therein connects the electrical control and alarm circuit between switches 602 and 606. A similar electrical cord 638 connects the circuit between switches 606 and 604.

The self-explanatory legends on the box 640 of FIG. 12 explain the functions of the various elements provided in the circuit, which will be described infra.

FIG. 13 shows, on an enlarged scale, a typical switch and illumination means assemblage of this preferred embodiment of the invention. The assemblage as shown in FIG. 13 is in the orientation of side rail assemblage of switch 604 and means 610 of FIG. 11, i.e. with the illumination member shedding light to the left onto the bed, however for purposes of convenience and to avoid needless repetition, the reference numerals of the other side rail assemblage, namely that of switch 602 and means 608, are shown in FIG. 13. Illumination means consisting of bulbs 642 and 644 and associated wiring, only partly shown in FIG. 13, are disposed within opposite ends of channel member 646, which together with inner fibre optic rod 648 serve to form the illumination means assemblage 608. Cover plate fittings 650 and 652 extend over and are mounted to cover respective bulb and associated wiring 642 and 644. An unnumbered second grouping of support and emplacement members, similar to members 618, 620, 622 and 624, is also shown in FIG. 13.

Referring now to FIG. 14, an alternative and preferred switch configuration is shown, as well as the upper horizontal section member 654 which joins the upper ends of members 618 and 620. Switch 602 is generally characterized by the provision of outer flexible plastic cover 656 which holds the switch per se, and which is mounted in channel member 658, the bottom of which is attached to the top surface of channel member 646. It will be evident to those skilled in the art that channel members 646 and 658 could alternatively be fabricated in practice as a single unit, by extrusion of aluminum, forming of plated steel strip, etc.

The internals of the switch 602 consist generally of an upper switch body 660 composed of a flexible plastic and within which is the actual upper switch which is actuated by low or moderate pressure, and a lower switch body 662 composed of a flexible plastic and within which is the actual lower switch which is actuated by heavy pressure (after the upper switch has first been actuated); the switch 662 would typically be actuated when a patient attempts to climb or crawl from the bed. A wood block 664 or the like is provided below switch 662 to provide firm and insulating support for the switch assemblage.

Returning to switch 660, an upper linear knob or protuberance 666 is provided to centralize actuation of the switch. Within switch 660 is an upper arcuate contact member 668 and a lower flat horizontal contact member 670. Both members 668 and 670 are mounted on side insulating mountings, and both members 668 and 670 are composed of copper or other metallic conductor of electricity. When a slight or moderate pressure is exerted on the upper surface of switch 602, typically on cover 656 above knob 666, since both members 656 and 660 are composed of flexible resilient plastic or the like, they deform downwards and the upper part of member 660 presses downwards against contact member 668, which bows downward and contacts member 670 to close the circuit and result in the appropriate signal e.g. a buzzer, light or illumination of the bed according to the circuitry.

Similar considerations apply with regard to lower switch 662 when a heavier downwards pressure is exerted against switch member 602, i.e. switch 660 moves downwards and upper internal flat horizontal contact member 672 of switch 662 moves downwards and contacts arcuate member 674 of switch 662 (which deforms upwards due to the provision of lower linear knob or protuberance 676), and upon contact of members 672 and 674 a further electrical circuit is completed and further devices are actuated, e.g. the emergency beeper.

FIG. 15 shows with clarity the mounting of the electric bulb 644 in a socket 678 within the end of channel 646. Wires 680 extend from socket 678 to plug 682 provided in channel 646 and wires 684 extend from switch member 602 to the plug 682.

FIGS. 16 and 17 show details of the mounting of the assemblage on a horizontal side rail of the bed, by means of strap 616.

An alternative illumination means is shown in FIG. 18. In this case, the fiber optic rod is omitted and instead the central channel cavity 686 of member 646 is empty. A plexiglass cover 688 is disposed in grooves 690 and 692 provided at the inner ends of the bifurcated channel member 646. The cover 688 prevents the entry of unwanted material or trash, e.g. cotton wadding, small bandages, scraps of food etc., into cavity 686, while also transmitting light onto the bed along the channel member 646.

FIG. 19 shows a preferred embodiment of control circuit for the invalid bed system. Assuming that the power switch 700 is in the down or "on" position, electric current, typically 12 volts A.C., will flow to the circuit. Wire 702 conducts current via wire 704 to beeper 706, and via wire 708 to relay 710, which when actuated cooperates with beeper 706. Referring to the heavy pressure switch 662, closing of this switch sends current through the relay 710 via wires 702, 708, 712, 714, 716, 718, 720, 722, 724, 726, 728, 730, 732, 734 and 736, so that current flow through relay 710 actuates the relay 710, which closes the normally open switch 738. This switch 738, when once closed, remains closed until reset via RESET switch button 641 of box 640, and when closed, switch 738 permits current to continuously flow through beeper 706 via wires 702, 704, 740, 714, 742, 744, 746, 726, 728, 730, 732, 734 and 736. Thus, the beeper sounds continuously until two things are accomplished, namely the opening of heavy pressure switch 662, i.e. return of the patient, either voluntarily or by the use of restraining force, to a normally reclining position in the bed; and manual opening of switch 738 via the RESET switch button 641 of box 640.

The control of current flow to the rail lights 642 and 644 is regulated by the RAIL LIGHT CONTROL section of box 640, which is shown in FIG. 19 as the illumination on/off switch 748 and the manually adjustable low-hi dimmer 750, the control knob 751 of which is shown in FIG. 12. Assuming that a decision is made to illuminate the bed by sending current through the rail lights, e.g. if the beeper 706 calls attention to trouble at the bed, switch 748 is moved to the on position. This closes a circuit through wires 752 and 754, switch 748, wire 756, dimmer 750 (which is characterized by the provision of a manually variable resistor element 758 as will be understood by those skilled in the art), wires 760 and 762, parallel wires 764 and 766 extending respectively to rail lights 642 and 644, wires 768 and 770 extending from these rail lights to wire 772 which extends to wire 722, which leads directly to the transformer via wires previously described, and the rail lights 642 and 644 are illuminated.

It is to be noted that the closing of switch 748 also energizes lamp 774 (which is in box 640 behind translucent switch 748), via circuit wires 752, 754, switch 748, wires 756, 776, 778 (which conducts the current to lamp 774), and wires 780, 782, 732, 734 and 736. It is also to be noted that closing of the main power switch 700 permanently energizes lamp 784 (which is in box 640 behind translucent switch 700) via wires 752, 786, 788, 782, 732, 734 and 736. The lighting of lamps 774 or 784 serves as an indicator that the respective switch is in the "on" position.

The circuit of the light pressure switch 660 will now be discussed. At the onset, switch 660 is provided for purposes of the patient's convenience in summoning a nurse or attendant. Thus, a light pressure applied by the patient, e.g. by placing a hand or arm on the switch 660, closes a circuit which actuates the call bell at the nurse's-station. In addition, provision is made in the circuit for utilization of an existing or "old" call bell actuation fitting by the patient, which is best shown as element 86 in FIG. 1 or element 458 in FIG. 7, to also actuate the call bell.

The Side Rail Call Bell switch (see box 640) is actually two switches 790 and 792, which operate in tandem. Closing these switches initially accomplishes the lighting of lamp 794 (which is in box 640 behind translucent switch 790-792), with current which flows from power switch 700 via wires 752, 754, 796, closed switch 790, wire 798 to lamp 794, and wires 800, 728, 730, 732, 734 and 736. In addition, since switch 792 will now be closed, a circuit is set up which is fully completed when the light pressure switch 660 is actuated (closed) by pressure from the hand, arm or leg of the patient. This circuit rings the call bell, as will appear infra.

In explanation of the function of the "Wall Plug" and "Old Call Bell" circuits, at the onset the individual components of these circuits will be detailed. The "Wall Plug" socket consists of three contacts, 802, 816 and 818; and the "Old Call Bell" socket also consists of three contacts, 822, 820 and 836. In each cae, two of the contacts form a normally closed circuit, the function of which will be explained infra.

The Relay actually consists of three elements, the relay coil 710, normally-open contacts 738, and normally-open contacts 828. The contacts are electro-mechanically connected to the relay coil, i.e., the contacts are closed and opened by respectively applying and removing power to the relay coil. On the "Old Call Bell" socket, 820 and 822 form a normally-closed circuit. When the existing or "old" call bell, e.g. element 86 of FIG. 1, is plugged into this socket, it mechanically opens the circuit between 820 and 822; this would be the normal operating condition of this circuit. When the patient actuates 86, this causes a connection to be made between 822 and 836, which rings the nurse's station via 802, 734, 822, 836, 826 and 818. If 86 is removed from the "Old Call Bell" socket for any reason, this causes a re-closure between 820 and 822, which rings the nurse's station via 802, 734, 822, 820, 824, 826 and 818. This function requires no power from control box 640.

The "Wall Plug" socket serves as the connecting point between the nurse's station and control box 640 via a cable with suitable plugs on each end. On the "Wall Plug" socket, 802 and 816 form a normally-closed circuit. When a suitable plug is inserted into this circuit, the plug mechanically opens the circuit between 802 and 816. Assuming that switch 700 is closed (this is necessary, since power must be turned on for proper operation of this circuit), the "Wall Plug" circuit works as follows. If the plug is removed from the socket, it causes a re-closure between 802 and 816, which creates a current path to actuate relay 710 via switch 700, 702, reset 641, 708, 712, 742, 834, 816, 802 and 736. It also provides a path to activate beeper 706 via switch 700, 702, reset 641, 704, 740, 714, 742, 834, 816, 802 and 736. When relay 710 energizes, it causes normally open contact 738 to close, which keeps relay 710 energized and beeper 706 active via 742, 738, 744, 746, 726, 728, 730, 732, 734 and 736 unless the circuit is properly reset. It should be noted that relay 710 also causes normally-open contact 828 to close, but this contact performs no effective function in the "Wall Plug" circuit. To reset the circuit, the plug must be re-inserted into the "Wall Plug" socket and the reset button 641 must be pressed. Pressing reset 641 breaks the current path which de-activates beeper 706, and de-energizes relay 710 which, in turn, causes contacts 738 and 828 to re-open.

The functions of the "Wall Plug" and "Old Call Bell" circuits, as explained supra, are meant as safety and auxiliary features to prevent tampering with the connections to control box 640.

It should be noted that there is a closed circuit via 828, 830, 814, 820, 822, 732, 730, 728, 726 and 746. This loop performs no function, except for 820 and 822 connection which rings nurse's station via 802, 734, 822, 820, 824, 826 and 818, which is part of the normal operation of control box 640 function (see explanation supra of "Old Call Bell" circuit operation), and has no effect on the operation of the control box 640.

Contact 828 is a parallel connection across light pressure switch 660. The purpose of this parallel connection is meant as a safety feature; if switch 792 is open (this effectively disconnects light pressure switch 660 from the circuit), and the heavy pressure switch 662 is actuated, this causes relay 710 to energize as described supra, and this closes normally open contact 828, which rings the nurse's station via 802, 734, 732, 730, 728, 726, 746, contact 828, 830, 814, 824, 826 and 818. This provision is necessary, since without it, if switch 792 is open, there would be no indication at nurse's station as to which room had activated the heavy pressure switch. If switch 792 is closed and the heavy pressure switch 662 is actuated, contact 828 and light pressure switch 660 operate in parallel and this is a safety feature insuring that the nurse's station is rung.

Referring now to FIGS. 20 and 22, operation of the nurse's station is the same as the original box except that the beeper is located at the nurse's station rather than in the patient's room. Additionally, there is an intercom hookup between the nurse's station and the patient's room, that is activated only when the call button (or the light pressure switch in the side rail) in the patient's room is pushed. The theory of operation of the nurse's station control center (FIGS. 20 and 22) consists of 40 individual room indicators 838, a patient alarm 840, intercom speaker 842, and a talk-listen switch 844; all of which are front panel mounted. Inside, there are 80 relays, consisting of 40 K1's, designated by 846; 40 K2's, designated by 848, and 40 intercom amplifiers 850.

Figure 23:
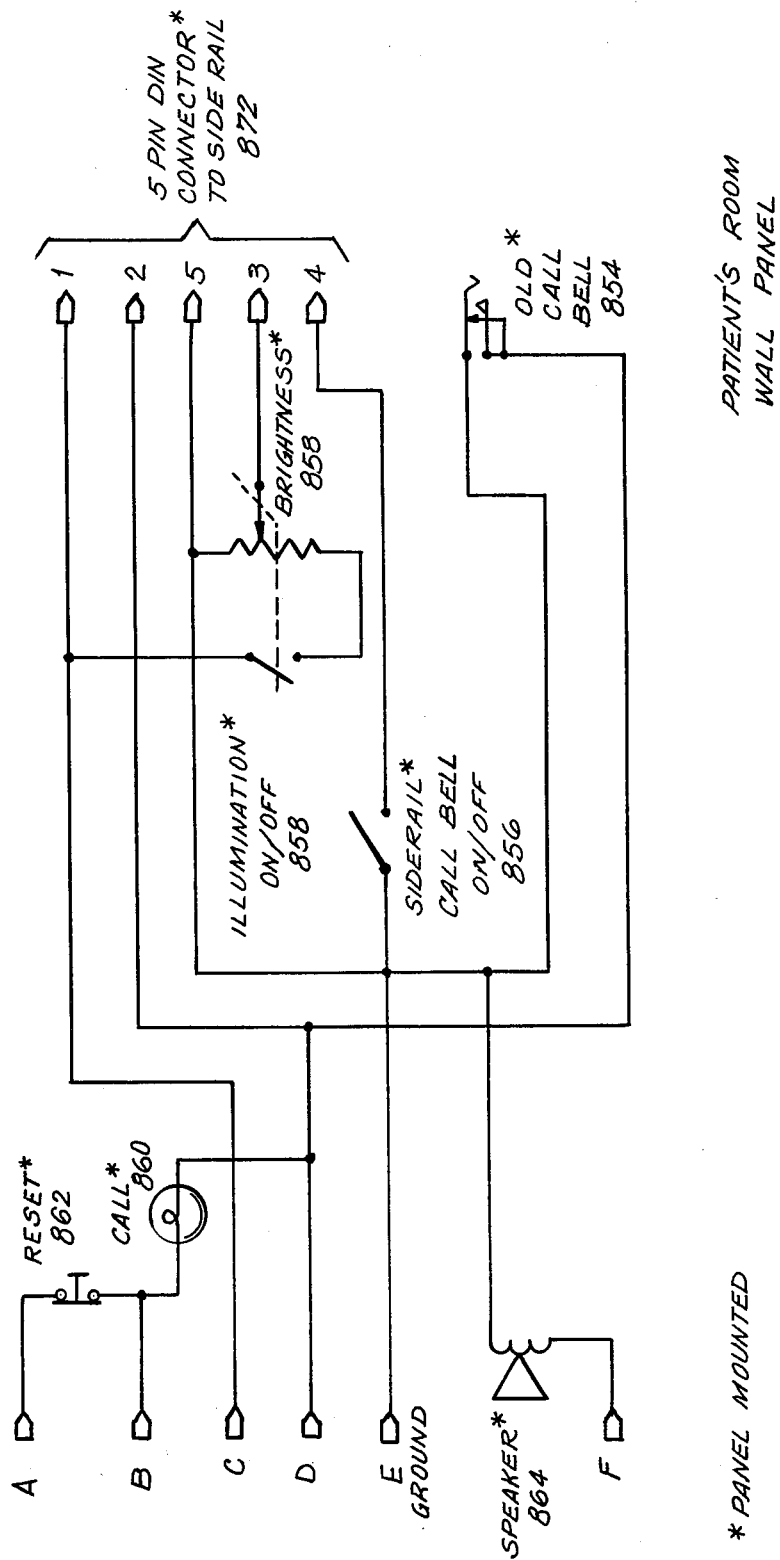
FIG. 23 is a wiring diagram relative to the room wall panel in the patient's room.

Referring now to FIGS. 21 and 23, the patient's room wall panel consists of two identical parallel operating channels (one for each bed). Each channel consists of one 5-pin connector 852 for plugging in to the side rail, one old call bell jack 854 for the handheld call button, one side rail call bell on/off switch 856, for turning off the light-pressure switch in the side rail, and one illumination control 858 with built-in on/off switch, which controls the brightness of the lamps in the side rails. In addition, the panel contains a call light 860 to indicate that the handheld call button, or the light pressure switch in the side rail, has been activated, a reset button 862, to reset the system after a call has been anwsered, and a speaker 864 for communicating with the nurse's station.

The nurse's station is capable of monitoring 40 rooms (80 beds). When a call to the nurse is made (by the patient pushing the handheld cell button plugged into 854, or pressing the light pressure switch in the side rail plugged into 852), closure is made between wires D and E (E shall supply ground), which illuminates lamp B of call indicator 838, and energizes relay 846 through wire B, the reset button 862 and wire A to the plus side of supply. When 846 energizes, the normally open contacts close. The 866 set of contacts connects the nurse's speaker 842 to the input of the intercom amplifier 850 through the talk/listen switch 844, which is a DPDT switch spring-loaded in the listen position. The set of contacts 868 connects the other side of the speaker 842 to the return side of supply B−. The output of the amplifier 850 is connected to the patient's speaker 864 via the talk/listen switch 844, and wire F. The other side of the speaker 864 is connected to wire E (ground). By activating the call button, the patient has given a visual display of the call (lamp 838) to the nurse and verbal communication can be carried on between patient and nurse, by the nurse's operation of the talk/listen switch 844. The call indicator (see FIG. 21) and the intercom connection cannot be disconnected unless the reset button 862 in the patient's room is depressed, which removes power from 846 and de-energizes it and extinguishes lamp 838 of the call indicator (FIG. 20).

When the heavy pressure switch in the side rail is activated, a closure is made between pins 1 and 5 of the DIN connector 872, which connects wire C to wire E which energizes relay 848 via wire B, the reset button 862, wire A and back to the plus supply. When the normally open contacts close, contact set 868 holds 848 energized and contact 866 energizes the beeper alarm 840 and lamp 838 of the call indicator (FIG. 20) via wire B, reset button 862, wire A and back to the plus supply. The beeper will remain on and the call indicator illuminated until the reset button 862 is depressed.

As various embodiments might be made in the above invention, and as various changes might be made in the embodiments above set forth, it is to be understood that all matter herein described or shown in the accompanying drawings is to be interpreted as illustrative and not in a limiting sense. Thus for example, it will be appreciated by those skilled in the art that alternative sources of electrical supply may be provided in practice, e.g. ordinary alternating electric current of 110–120 or 220 volts; a power-driven generator or alternator, or a suitable battery or bank of batteries.

Having thus described the invention, there is claimed as new and desired to be secured by Letters Patent:

1. A warning system for a hospital bed comprising a hospital bed, said hospital bed including at least two opposed side rails, a weight sensitive electric switch located on the top of at least one side rail, a first electric warning device located in the vicinity of said hospital bed, a second electric warning device located at a desired location, a source of electric power, means for selectively connecting said source of power to either of said warning devices or for connecting said source of power to both said first warning device and said second warning device upon said weight switch being activated, a patient call button, means for connecting said patient call button to said selective connecting means so said patient call button can be used to selectively connect said source of electric power to both said first electric warning device and said second electric warning device or only to said first electric warning device or only to said second electric warning device, a third warning device, said weight sensitive switch including a first pair of contacts and a second pair of contacts, said first pair of contacts being closed upon sensing a first predetermined force and said second pair of contacts being closed upon sensing a second predetermined force, said second predetermined force being greater than said first predetermined force, and means connecting said third warning device to said source of electric power when said second pair of contacts close.

2. A warning system according to claim 1 wherein a second weight sensitive electric switch is located over the remaining side rail, said second switch being identical to said first switch, and means connecting said second weight sensitive electric switch to said selective connecting means.

3. A warning system according to claim 2 wherein said hospital bed includes a foot rail, and a third weight sensitive electric switch located on top of said foot rail, said third weight sensitive electric switch being identical to said first and second weight sensitive electric switches, and connected to said selective connecting means.

4. A warning system according to claim 3 wherein said selective connecting means includes a first circuit leg and a second circuit leg, means for selectively connecting said source of electric power to both said first circuit leg and said second circuit leg or individually to said first circuit leg or individually to said second circuit leg, said first warning device being in said first circuit leg and the first pair of contacts of said first, second and third weight sensitive electric switches being connected to said first warning device.

5. A warning device according to claim 4 wherein the second pair of contacts of said first, second and third weight sensitive electric switches are in said second circuit leg, said third warning device being connected to said second pair of contacts of said first, second and third weight sensitive switches.

6. A warning system according to claim 4 wherein said second warning device is connected to said first circuit leg and to said second circuit leg.

7. A warning system according to claim 6 further including a control box, said control box including a first, second, third and fourth sockets connected to said first circuit leg, said patient call button connected to said first socket and said first pair of contacts of said first, second and third weight sensitive electric switches being connected to said second, third and fourth sockets, respectively.

8. A system according to claim 7 wherein said control box includes at least one light socket, said one light socket being connected to said source of electric power and illuminating means for illuminating said hospital bed being connected to said first light socket..

9. A warning system according to claim 7 wherein said control box includes fifth, sixth and seventh sockets, said second pair of contacts of said first, second and third weight sensitive electric switches being connected to said fifth, sixth and seventh sockets, respectively and said fifth, sixth and seventh sockets connected to said third warning device.

10. In a hospital having a bed with at least one rail, a nurse's station located at a distance from said bed, a wall terminal in proximity to said bed and means connecting said wall terminal to said nurse's station, the warning system combination of first and second elongated pressure sensitive switches on top of said rail, said first pressure sensitive switch being actuatable by light pressure, said second pressure sensitive switch being actuatable by heavy pressure, a first warning device at said nurse's station, a first lead connecting said first warning device to said connecting means, a control box, a second warning device in said control box, a second lead connecting said control box to said switches, and a third lead connecting said control box to said wall terminal, so that actuation of said first switch serves to actuate said first warning device and actuation of said second switch serves to actuate said second warning device.

11. The warning system of claim 10 in which lighting means are provided on said rail below said switches, said lighting means being connected to the control ox through the second lead, together with means in the control box to regulate said lighting means.

12. The warning system of claim 10 in which switch means are provided in the control box to control the connection between the first switch and the first warning device.

13. The warning system of claim 10 together with a call button at the bed and a lead extending from the button to the control box, so that pressing of the button actuates the first warning device.

14. The warning system of claim 10 in which means are provided to continuously actuate the second warning device when one actuated by the closing of the second switch, together with pressure-sensitive reset means to interrupt and stop the acutation of the second warning device until the second switch is again closed.

15. In a hospital having a bed with at least one rail, a nurse's station located at a distance from said bed, a wall terminal in proximity to said bed and means connecting said wall terminal to said nurse's station, the warning system combination of first and second elongated pressure sensitive switches on top of said rail, said first pressure sensitive switch being actuatable by light pressure, said second pressure sensitive switch being actuatable by heavy pressure, a first warning device at said nurse's station, a first lead connecting said first warning device to said connecting means, a second warning device at said nurse's station, and a second lead connecting said second warning device to said connecting means so that actuation of said first switch serves to actuate said first warning device, and actuation of said second switch serves to actuate said second warning device.

* * * * *